United States Patent [19]
Aust et al.

[11] Patent Number: 5,454,827
[45] Date of Patent: Oct. 3, 1995

[54] SURGICAL INSTRUMENT

[76] Inventors: Gilbert M. Aust, 14 Asbury La., Huntsville, Ala. 35802; Timothy E. Taylor, HC 66 Box 203, Paint Rock, Ala. 35764

[21] Appl. No.: 248,507

[22] Filed: May 24, 1994

[51] Int. Cl.⁶ ................................. A61B 17/00
[52] U.S. Cl. .................. 606/170; 606/174; 606/205; 128/751
[58] Field of Search .................. 606/51, 52, 108, 606/174, 205–211, 198, 170; 128/3, 4, 6, 751–755

[56] References Cited

U.S. PATENT DOCUMENTS

| | | |
|---|---|---|
| 4,499,899 | 2/1985 | Lyons . |
| 4,517,977 | 5/1985 | Frost . |
| 4,649,919 | 3/1987 | Thimsen et al. . |
| 4,763,669 | 8/1988 | Jaeger ................. 606/174 |
| 4,834,069 | 5/1989 | Umeda . |
| 4,834,729 | 5/1989 | Sjostrom . |
| 4,880,015 | 11/1989 | Nierman ................. 128/751 |
| 5,025,804 | 6/1991 | Kondo . |
| 5,143,475 | 9/1992 | Chikama . |
| 5,178,129 | 1/1993 | Chikama et al. . |
| 5,209,747 | 5/1993 | Knoepfler ................. 606/52 |
| 5,295,990 | 3/1994 | Levin ................. 128/751 |
| 5,330,502 | 7/1994 | Hassler et al. ................. 606/174 |

Primary Examiner—Stephen C. Pellegrino
Assistant Examiner—William Lewis
Attorney, Agent, or Firm—Tarolli, Sundheim & Covell

[57] ABSTRACT

An arthroscopic or endoscopic surgical instrument includes a manually engageable handle, a rigid stem section extending from the handle, and tissue engaging means for engaging tissue. The tissue engaging means includes first and second tissue engaging members. The first tissue engaging member is pivotable relative to the second tissue engaging member to engage tissue between the first and second tissue engaging members. An articulated shaft is connected between the stem section and the tissue engaging means and supports the tissue engaging means for movement between a plurality of orientations relative to the stem section. First actuator means is connected with the handle for bending the articulated shaft to change the orientation of the tissue engaging means relative to the stem section from a first orientation to a second orientation. Second actuator means is connected with the handle and with the first tissue engaging member for effecting pivotal movement of the first tissue engaging member relative to the second tissue engaging member to engage tissue between the first and second tissue engaging members when the tissue engaging means is in any of its plurality of orientations relative to the stem section.

13 Claims, 5 Drawing Sheets

SURGICAL INSTRUMENT

BACKGROUND OF THE INVENTION

The present invention relates to a surgical instrument and more particularly, to an arthroscopic/endoscopic surgical instrument which may be used to remove or otherwise treat tissue in a joint or other body space.

Surgical instruments which may be used to remove tissue or perform other operations on tissue are disclosed in U.S. Pat. Nos. 4,499,899; 4,517,977; 4,649,919; 4,763,669; and 4,834,729. The surgical instruments disclosed in these patents have stem sections which extend outwardly from a handle. A cutting tool or other device is disposed at the outer end of the stem section. The stem section is rigid, and the cutting tool or other device can not be moved in different planes relative to the stem section.

SUMMARY OF THE INVENTION

The present invention is a surgical instrument comprising a manually engageable handle, a rigid stem section extending from the handle, and tissue engaging means for engaging tissue. The tissue engaging means includes first and second tissue engaging members. The first tissue engaging member is pivotable relative to the second tissue engaging member to engage tissue between the first and second tissue engaging members. An articulated shaft is connected between the stem section and the tissue engaging means, and supports the tissue engaging means for movement between a plurality of orientations relative to the stem section. First actuator means is connected with the handle for bending the articulated shaft to change the orientation of the tissue engaging means relative to the stem section from a first orientation to a second orientation. Second actuator means is connected with the handle and with the first tissue engaging member for effecting pivotal movement of the first tissue engaging member relative to the second tissue engaging member to engage tissue between the first and second tissue engaging members when the tissue engaging means is in any of its plurality of orientations relative to the stem section.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF PREFERRED EMBODIMENTS OF THE INVENTION

Figure 1:
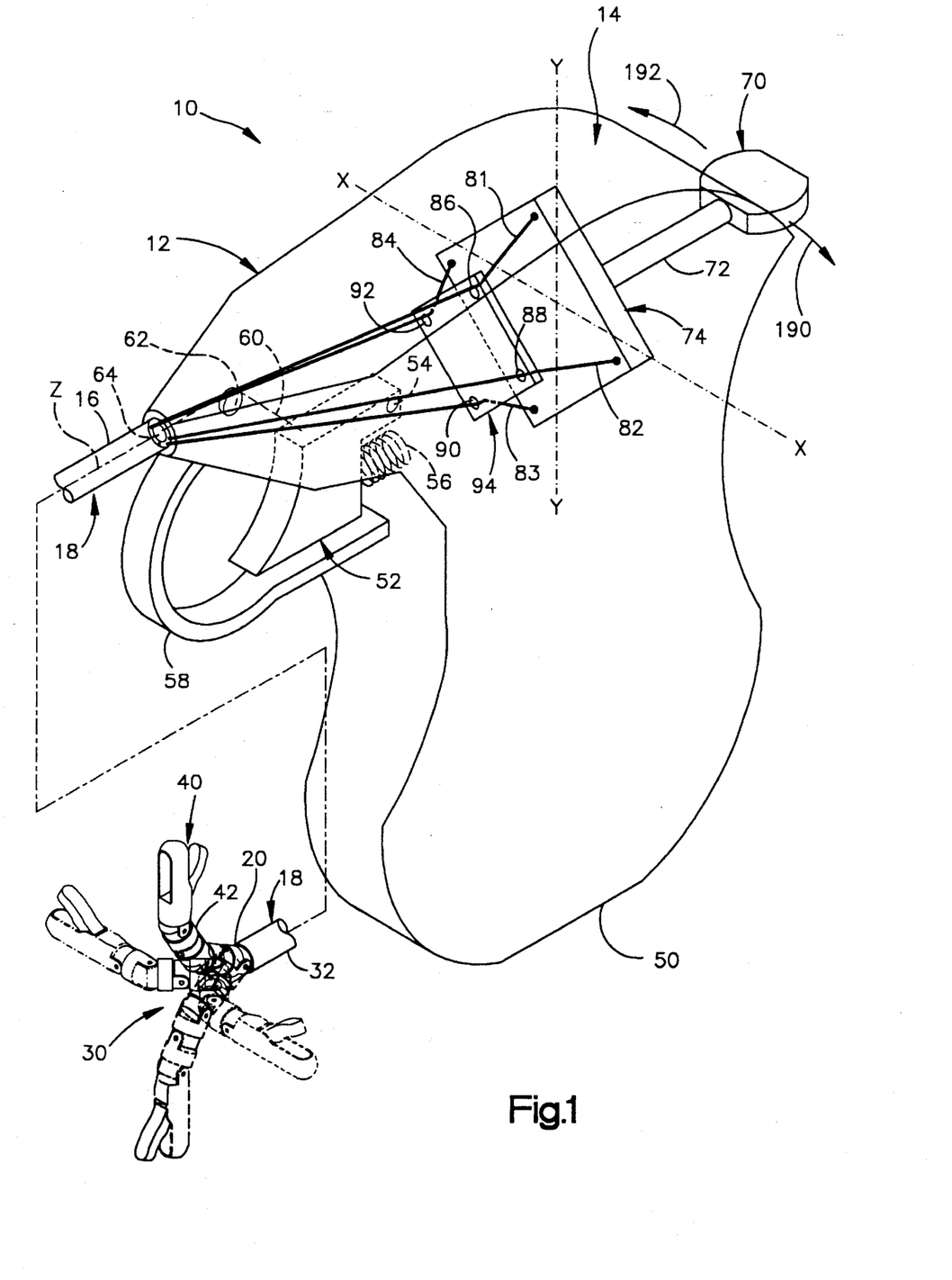
FIG. 1 is a schematic illustration of a surgical instrument constructed in accordance with the present invention.

The present invention relates to a surgical instrument and in particular to a surgical instrument which may be used to remove tissue or perform other operations on tissue. The present invention is applicable to various surgical instrument constructions. As representative of the present invention, FIG. 1 illustrates a surgical instrument 10.

The surgical instrument 10 includes generally a handle 12 with an actuator assembly 14. A proximal end portion 16 of a rigid stem section 18 is fixed to the handle 12. A proximal end portion 20 of an articulated stem section 30 is connected with a distal end portion 32 of the rigid stem section 18. A basket cutter 40 is connected with a distal end portion 42 of the articulated stem section 30.

The handle 12 (FIG. 1) includes a main body portion 50 which is configured to be manually gripped by a person's hand. A trigger 52 is connected at 54 to the main body portion 50 for pivotal movement relative to the main body portion. A spring 56 connected between the trigger 52 and the main body portion 50 biases the trigger to an unactuated position shown in FIG. 1. A trigger guard 58 blocks unintended contact with the trigger 52.

A proximal end portion of a control wire 60 is connected with the trigger 52. The control wire 60 extends from the trigger 52 over a guide indicated schematically at 62 and thence into a central passage 64 in the rigid stem section 18. The control wire 60, in a manner to be described below, extends through the rigid stem section 16 and through the articulated stem section 30 and is connected with the basket cutter 40.

The actuator assembly 14 is mounted in the main body portion 50 of the handle 12. The actuator assembly 14 is illustrated only schematically. It should be understood that other types of actuator assemblies capable of providing the multi-directional control provided by the actuator assembly 14 can be substituted. Thus, the actuator assembly 14 is illustrative of the various types of actuator assemblies which can be used to provide the actuation force for bending the articulated stem section 30 in multiple planes as indicated in FIG. 1.

The actuator assembly 14 (FIGS. 1 and 2) includes a control lever 70 which projects from the handle main body portion 50. The control lever 70 is supported by a rod 72 which is fixed for movement with a control plate 74. The control plate 74 is mounted in the handle main body portion 50 in a suitable manner, not shown, for simultaneous pivotal movement about both an X axis and a perpendicular Y axis as indicated in FIG. 1.

The proximal ends of four actuator wires 81, 82, 83, and 84 are fixed to respective corners of the control plate 74. The four actuator wires 81, 82, 83, and 84 extend through respective guide openings 86, 88, 90, and 92 in a guide plate 94. The guide plate 94 is fixed in position in the handle main body portion 50 in a manner not shown. The actuator wires 81–84 extend from the guide plate 94 into the central passage 64 in the rigid stem section 18. The actuator wires 81–84, in a manner to be described below, pass through the rigid stem section 18 and are connected with the basket cutter 40 which is mounted on the end of the articulated stem section 30.

The rigid stem section 18 is a hollow tubular member which extends between and interconnects the handle 12 and the articulated stem section 30. The rigid stem section 18 is cylindrical in configuration with parallel cylindrical inner and outer surfaces 96 and 98. The cylindrical inner surface 96 defines the central passage 64 in the rigid stem section 16. The control wire 60 and the four actuator wires 81, 82, 83, and 84 extend through the central passage 64 of the rigid stem section 16. The rigid stem section 16 defines a Z axis of the surgical instrument 10 which extends perpendicular to the X and Y axes.

The articulated stem section 30 is made of a plurality of links which are pivotally interconnected to enable controlled movement of the basket cutter 40 in any selected direction and to any position off the Z axis. The links are rigid, generally cylindrical hollow members through which the control wire 60 and the actuator wires 81–84 extend.

Figure 3:
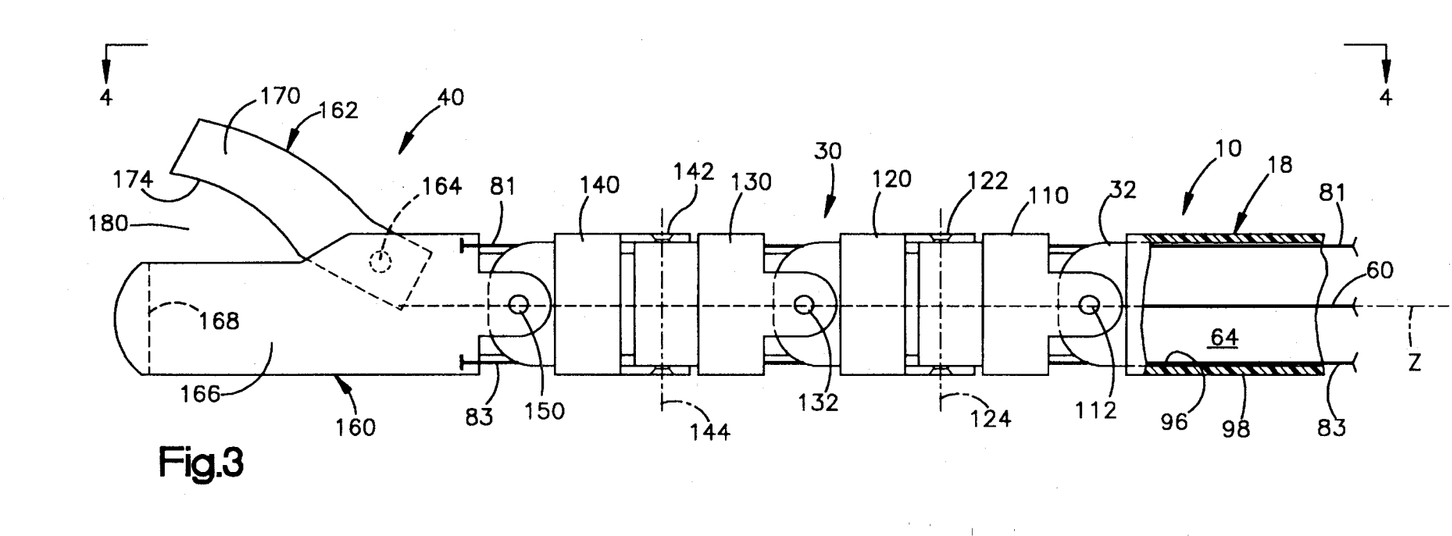
FIG. 3 is an enlarged schematic side elevational view of an articulated stem section of the surgical instrument of FIG. 1.
Figure 4:
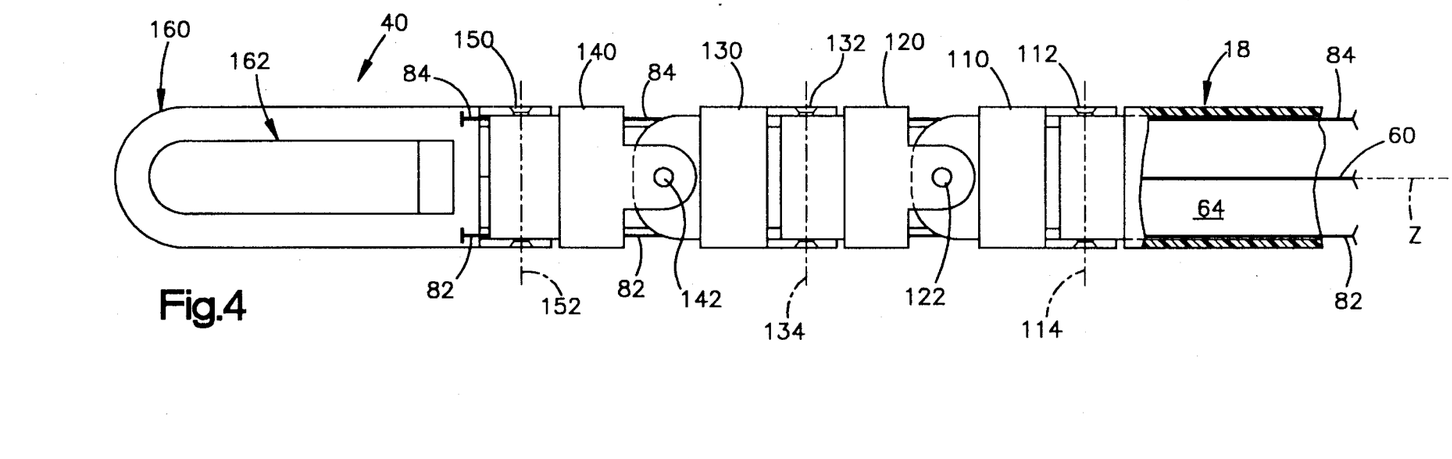
FIG. 4 is an enlarged schematic top plan view of the articulated section.

The plurality of links in the articulated stem section 30 includes a first link 110 which is connected by a first pivot joint 112 to the distal end portion 32 of the rigid stem section 18. The first pivot joint 112 defines a first pivot axis 114 which, when the articulated stem section 30 is linear and extends along the Z axis, extends in a direction parallel to the X axis and perpendicular to the Z axis.

A second link 120 is connected by a second pivot joint 122 to the first link 110. The second pivot joint 122 defines a second pivot axis 124. When the articulated stem section 30 is linear and is aligned along the Z axis, the second pivot axis 124 extends in a direction parallel to the Y axis and perpendicular to the Z axis.

A third link 130 is connected by a third pivot joint 132 to the second link 120. The third pivot joint 132 defines a third pivot axis 134 which extends in a direction parallel to the first pivot axis 114.

A fourth link 140 is connected by a fourth pivot joint 142 to the third link 130. The fourth pivot joint 142 defines a fourth pivot axis 144 which extends in a direction parallel to the second pivot axis 124.

The basket cutter 40 is connected by a fifth pivot joint 150 to the fourth link 140. The fifth pivot joint 150 defines a fifth pivot axis 152 which extends in a direction parallel to the first pivot axis 114.

The basket cutter 40 includes a fixed jaw 160 and a movable jaw 162. A pivot joint 164 connects the movable jaw 162 with the fixed jaw 160 for pivotal movement relative to the fixed jaw.

The fixed jaw 160 includes a side wall 166 which defines an open-ended chamber 168 in the fixed jaw. The movable jaw 162 includes a side wall 170 which extends around and defines a chamber 172. The side wall 170 has a cutting edge 174 presented toward the side wall 166 of the fixed jaw 160. The fixed jaw 160 and the movable jaw 162 define between them a mouth or gap 180 within which human tissue can be received and grasped upon pivotal movement of the movable jaw toward the fixed jaw.

The four actuator wires 81–84 extend through the open centers of the links 110, 120, 130, and 140. The distal ends of the actuator wires 81–84 are connected with the fixed jaw 160 of the basket cutter 40. The wires 81–84 are connected at locations evenly spaced 90° apart around the periphery of the fixed jaw 160. Directional movement and positioning of the basket cutter 40 via the articulated stem section 30 are controlled by the tension on the actuator wires 81–84 as set by the actuator assembly 14.

Figure 2:
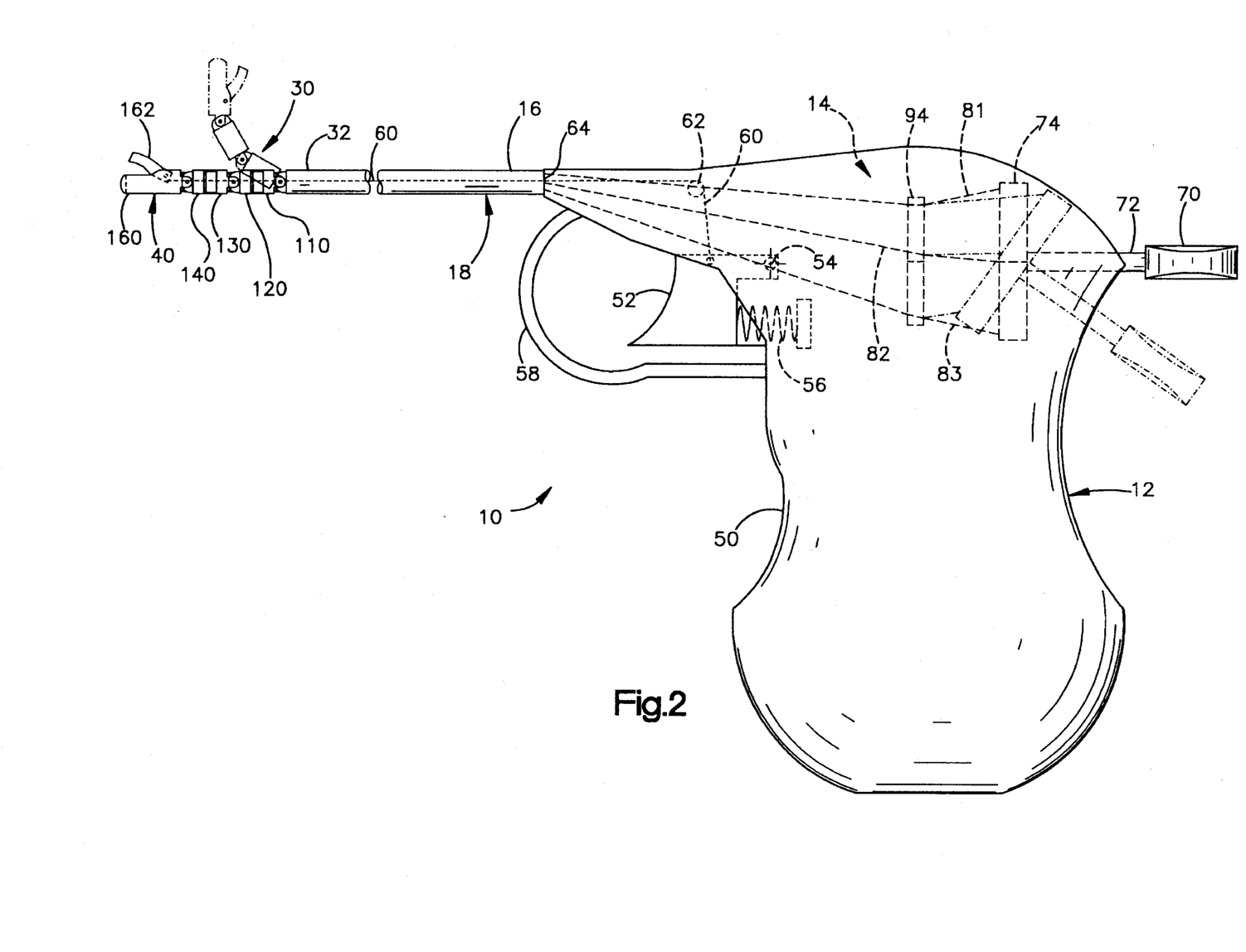
FIG. 2 is a schematic side elevational view of the instrument of FIG. 1.
Figure 5:
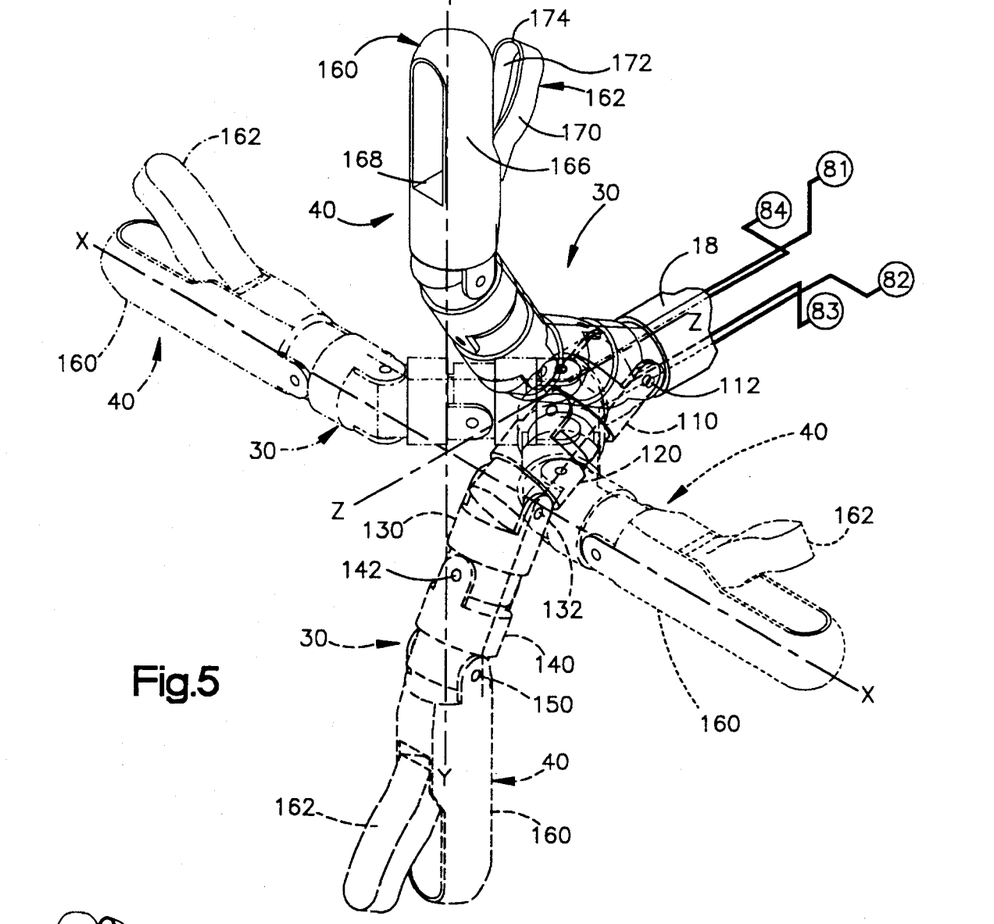
FIG. 5 is a schematic illustration depicting deflection of the articulated section in one of four directions.

Thus, when the control lever 70 (FIGS. 1 and 2) is in the centered position shown in solid lines in FIG. 2, the articulated stem section 30 is linear, and it and the basket cutter 40 are aligned along the Z axis as shown in FIG. 5. Downward movement of the control lever 70 as seen in FIG. 1 and 2, from the position shown in solid lines in FIG. 2 to the position shown in dashed lines in FIG. 2, causes the control plate 74 to pivot relative to the handle main body portion 50 about the X axis (FIG. 1). This pivoting movement of the control plate 74 tensions the actuator wire 81 and releases the tension on the opposite actuator wire 83. This change in the tension on the wires 81 and 83 is transmitted through the wires 81 and 83 into the basket cutter 40. The increase in tension on the wire 81 acts to attempt to pull the basket cutter 40 toward the handle 12. The articulated stem section 30 bends as the links 110, 120, 130, and 140 pivot relative to the rigid stem section 30. The fixed jaw 160 of the basket cutter 40 thus moves upward off the Z axis in a direction toward the Y axis.

Figure 5A:
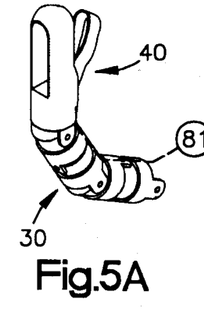
FIG. 5a is a schematic view of a portion of FIG. 5 showing the articulated section bent in a first direction.

If the control lever 70 is, in this manner, moved to its lowest position, the basket cutter 40 moves to its highest position, aligned with the Y axis, as illustrated in solid lines in FIG. 5 and as also illustrated in FIG. 5a. The basket cutter 40 is, by appropriate positioning of the control lever 70 within its range of pivoting movement about the X axis, movable to any position between the aligned position along the Z axis and the full upward position shown in FIG. 5a. This occurs as a result of the bending of the articulated stem section 30.

Figure 5B:
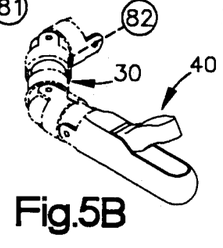
FIG. 5b is a view similar to FIG. 5a showing the articulated section bent in a second direction.
Figures 5C, 5D:
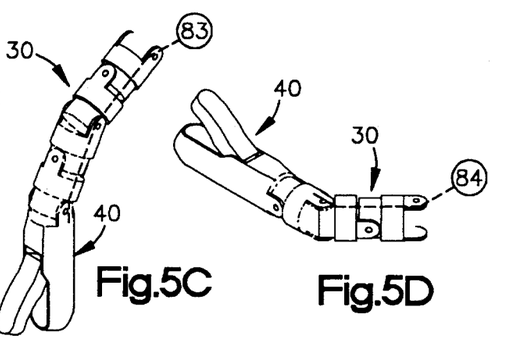
FIG. 5c is a view similar to FIG. 5a showing the articulated section bent in a third direction.
FIG. 5d is a view similar to FIG. 5a showing the articulated section bent in a fourth direction.

If the control lever 70 is moved in the opposite direction, the basket cutter 40 moves also in the opposite direction. Thus, movement of the control lever 70 in an upward direction as viewed in FIGS. 1 and 2, from the position shown in solid lines in FIG. 2, causes the control plate 74 to pivot relative to the handle main body portion 50 about the X axis (FIG. 1). This pivoting movement of the control plate 74 tensions the actuator wire 83 and releases the tension on the opposite actuator wire 81. This change in the tension of the wires 81 and 83, whose ends are connected with the fixed jaw 160 of the basket cutter 40, causes the basket cutter to move downward off the Z axis in a direction toward a position as shown in FIG. 5c. The position of the control lever 70 is continuously adjustable among a plurality of positions between the position aligned with the Z axis as shown in FIG. 2 in solid lines and its uppermost position. As described above, the position of the basket cutter 40 is also continuously adjustable between a position aligned with the Z axis and a lowermost position as illustrated in FIG. 5c, and any position in between.

In a similar manner, horizontal movement of the control lever 70 relative to the handle main body portion 50 results in corresponding horizontal movement of the basket cutter 40. Thus, movement of the control lever 70 in the direction indicated by the arrow 190 (FIG. 1) causes the control plate 74 to pivot about the Y axis (FIG. 1). The tension on the actuator wire 84 is increased and, simultaneously, tension on the actuator wire 82 is decreased. These changes in tension of the actuator wires are transmitted into the fixed jaw 160 of the basket cutter 40. The articulated stem section 30 bends and the basket cutter 40 moves horizontally, that is, in the plane defined by the X and Z axes as illustrated in FIG. 5, toward the position illustrated in FIG. 5d. The range of movement of the basket cutter 40 in this direction is continuous, so the basket cutter 40 can be placed in any position between a position aligned with the Z axis and a position aligned with the X axis as illustrated.

Again, movement of the control lever 70 in the opposite direction as indicated by the arrow 192 in FIG. 1 tensions the actuator wire 82 and releases the tension on the actuator wire 84. The change in tension on the actuator wires 82 and 84 is transmitted to the fixed jaw 160 of the basket cutter 40. The articulated stem section 30 bends and the basket cutter 40 moves in the plane defined by the X and Z axes from a position aligned with the Z axis toward a position aligned with the X axis. The basket cutter may, by appropriate positioning of the control lever 70, be placed in any position between a position aligned with the Z axis and a position aligned with the X axis as illustrated in FIG. 5b.

It should be understood that any combination of the foregoing four movements is possible. Thus, the basket cutter 40 is movable not only in the planes illustrated in FIGS. 5-5d but also to any intermediate position in any combination of the planes. The basket cutter 40 can be moved upward while it is being moved to the left or right. The basket cutter 40 can be moved downward while it is being moved to the left or right.

The positioning of the movable jaw 162 of the basket cutter 40 relative to the fixed jaw 160 is controlled by tension on the control wire 60 as set by the trigger 52. When the trigger 52 is in the unactuated position as illustrated in FIGS. 1 and 2, the tension on the control wire 60 is lowest and the basket cutter 40 is open. The movable jaw 162 is biased by a spring (not shown) to an open position as illustrated in the Figures spaced apart from the fixed jaw 160 and defining between them a gap 180.

To cut or remove tissue with the basket cutter 40, the basket cutter is maneuvered so that the tissue is disposed in the gap 180 between the fixed and movable jaws 160 and 162. The trigger 52 is pulled, against the bias of the spring 56. The trigger 52 pivots about the pivot axis 54, tensioning the control wire 60. The distal end of the control wire 60 is connected with the movable jaw 162 of the basket cutter 40, as illustrated in FIG. 3. Tensioning of the control wire 60 thus results in pivotal movement of the movable jaw 162 from the open position shown in FIG. 3 to a closed position (not shown).

Tissue which is during this movement disposed in the gap 180 is engaged by the cutting edge 174 on the side wall 170 of the movable jaw 162. The cutting edge 174 on the side wall 170 of the movable jaw 162 slides against the side wall 166 of the fixed jaw 160. The basket cutter 40 can then be removed from the operating location to gain access to the tissue. Releasing the pressure on the trigger 52 causes the trigger to return to the position shown in FIG. 1 under the influence of the spring 56. This lowers the tension on the control wire 60. The basket cutter 40 opens and releases the tissue.

It should be understood that the basket cutter 40 is actuatable independently of its position as set by the articulated stem section 30. Thus, the movable jaw 162 may be moved relative to the fixed jaw 160 regardless of the overall position of the basket cutter 40 as set by the articulated stem section 30. It should also be understood that the surgical instrument 10 is preferably used in arthroscopic or endoscopic surgery to remove or treat human tissue at subsurface locations such as in a knee joint or in the spine.

Figure 6:
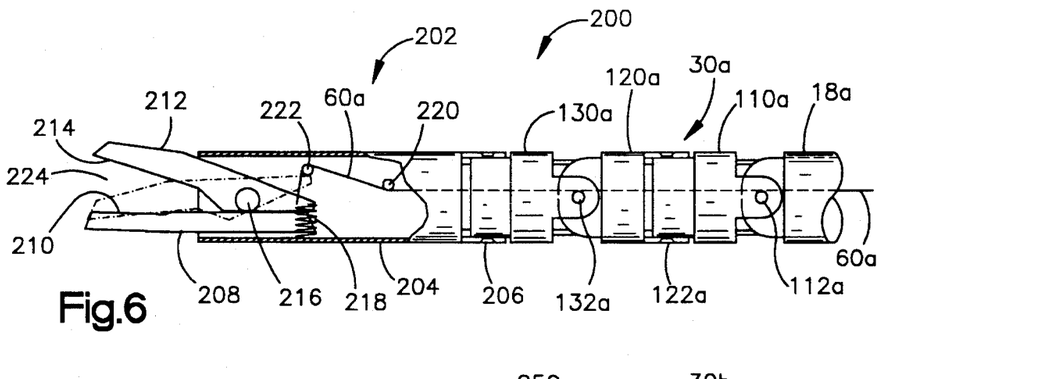
FIG. 6 is a schematic side view, partly in section, showing a second surgical instrument, which includes a scissors assembly mounted on an articulated section.

FIG. 6 illustrates a surgical instrument 200 in accordance with a second embodiment of the present invention. In place of the basket cutter 40, the surgical instrument 200 includes a scissors assembly 202 mounted on the end of an articulated stem section 30a. The articulated stem section 30a is identical to the articulated stem section 30 illustrated in FIGS. 1-5.

The scissors assembly 202 includes a base 204 connected by a pivot joint 206 to a link 130a of the articulated stem section 30a. A fixed blade 208 is rigidly mounted on the base 204. The fixed blade 208 has a cutting edge 210. A movable blade 212 having a cutting edge 214 is pivotally mounted at 216 to the base 204. A spring 218 biases the movable blade 212 away from the fixed blade 208 to an open position as illustrated in FIG. 6.

A control wire 60a extends through the open center of the articulated stem section 30a. The control wire 60a is trained over pins 220 and 222 and is connected with the movable blade 212. Tensioning the control wire 60a causes pivotal movement of the blade 212 from the open position shown in solid lines in FIG. 6 to the cutting position shown in dot-dash lines. Tissue which is disposed in the gap 224 between the blades 208 and 212 is cut during such pivotal movement. Upon release of tension on the control wire 60a, the spring 218 moves the movable blade 212 back to the open position. Pivotal movement of the movable scissors blade 212 in either direction can be accomplished in any position of orientation of the scissors assembly 202 as provided by the bending of the articulated stem section 30a.

Figure 7:
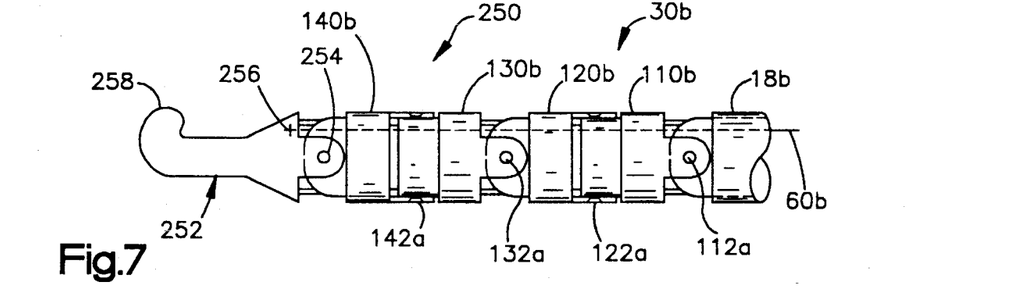
FIG. 7 illustrates a surgical instrument including a probe or knife mounted on an articulated section.

FIG. 7 illustrates a surgical instrument 250 in accordance with a third embodiment of the invention. The surgical instrument 250 includes an articulated stem section 30b which is identical to the articulated stem section 30 illustrated in FIGS. 1-5. A one-piece instrument 252 which can be either a probe or a knife is mounted on the end of the articulated stem section 30b. A pivot joint 254 provides for pivotal movement of the instrument 252 relative to the final link 140b of the articulated stem section 30b. A control wire indicated schematically at 60b extends through the open center of the links into the articulated stem section 30b. The control wire 60b terminates at a connection 256 fixed to the instrument 252.

Upon tensioning the control wire 60b, the instrument 252 pivots about the pivot joint 254 in an upward direction as viewed in FIG. 7. Upon release of tension on the control wire 60b, a spring or other biasing means (not shown) returns the instrument 252 to its illustrated position. The instrument 252 is actuatable in this manner when in any position of orientation of the articulated stem section 30b.

If the instrument 252 is a knife, it possesses a cutting edge as indicated at 258. Alternatively, any other one-piece instrument in the nature of a probe or a knife could be substituted.

Figure 8:
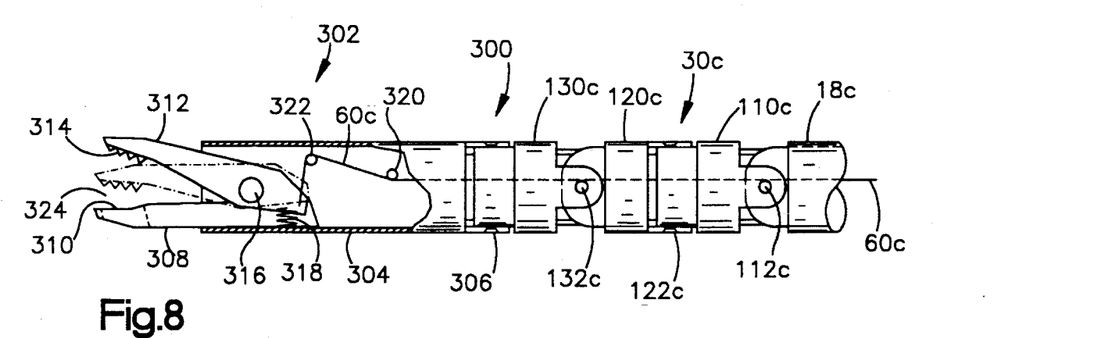
FIG. 8 illustrates a surgical instrument including a basket cutter of an alternative construction mounted on the articulated section.

FIG. 8 illustrates a surgical instrument 300 in accordance with a fourth embodiment of the invention. The surgical instrument 300 includes a basket cutter 302 mounted on a distal end of an articulated stem section 30c. The articulated stem section 30c is identical to the articulated stem section 30 illustrated in FIGS. 1-5. The basket cutter 302 differs somewhat from the basket cutter 40 illustrated in FIGS. 1-5.

The basket cutter 302 includes a base 304 connected by a pivot joint 306 to the final link 130c of the articulated stem section 30c. A jaw 308 is fixed to the base 304. The fixed jaw 308 has an open cutting area indicated schematically at 310. The basket cutter 302 includes a movable jaw 312 having cutting teeth indicated schematically at 314. The movable jaw 312 is connected at a pivot joint 316 for pivotal movement relative to the fixed jaw 308. A spring 318 biases the movable jaw 312 into an open position as illustrated in solid lines in FIG. 8.

A control wire 60c is trained around pins 320 and 322 fixed to the base 304 and is connected with the movable jaw 312. Tension on the control wire 60c pivots the movable jaw 312 from the position shown in solid lines in 312, against the biasing effect of the spring 318, and into a position adjacent the fixed jaw 308. Tissue which is during this pivotal movement disposed in the gap 324 between the teeth 314 and the open area 310 is cut and retained in the basket.

The basket cutter 302 may then be withdrawn from the body. Release of tension on the control wire 60c results in movement of the movable jaw 312, under the influence of the biasing spring 318, into the open position to allow removal of the captured tissue. The basket cutter 302 is actuatable between the open and closed positions when in any orientation of the articulated stem section 30c.

Figure 9:
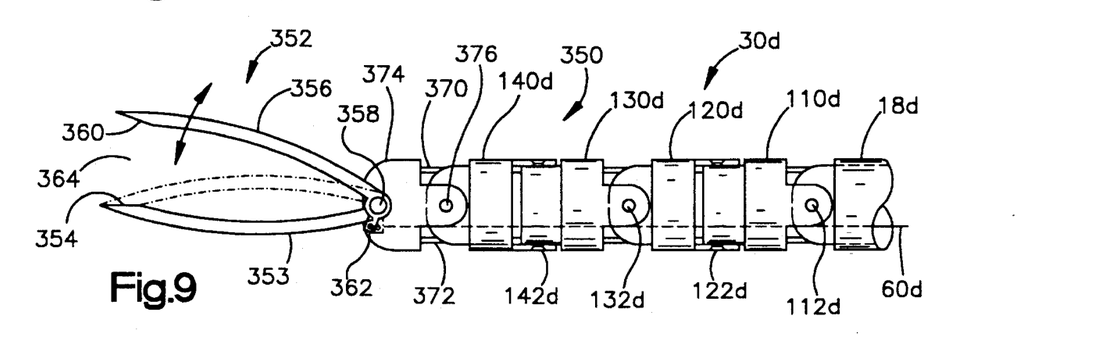
FIG. 9 illustrates a surgical instrument including a forceps/grasper assembly mounted on the articulated section.

FIG. 9 illustrates a surgical instrument 350 in accordance with a fifth embodiment of the invention. The surgical instrument 350 includes a forceps/grasper assembly 352 connected to the distal end portion of a articulated stem section 30d. The articulated stem section 30d is identical to the articulated stem section 30 illustrated in FIGS. 1–5. The forceps/grasper assembly 352 include a fixed jaw 353 having a grasping surface 354. A movable jaw 356 is pivotally connected at 358 to the fixed jaw 353. The movable jaw 356 has a grasping surface 360 which is opposable to the grasping surface 354 on the fixed jaw 353. A control wire 60d is connected to a tab 362 fixed to the movable jaw 356.

Tensioning of the control wire 60d results in pivotal movement of the movable jaw 356 from the position shown in solid lines in FIG. 9 to the position shown in dot-dash lines in FIG. 9. During such pivotal movement, tissue which is disposed in a gap 364 between the grasping surfaces 354 and 360 is captured between the fixed and movable jaws 353 and 356. The forceps/grasper assembly 352 is actuatable regardless of the orientation of the articulated stem section 30d.

Actuator wires 370 and 372 (FIG. 9) are connected with a base 374 of the forceps/grasper assembly 352. The actuator wires 370 and 372 are movable, in a manner as described with reference to FIGS. 1–5, to position the forceps/grasper assembly 352 about an axis relative to the final link 140d of the articulated stem section 30d. Appropriate tensioning of the actuator wires 370 and 372 causes the forceps/grasper assembly 352 to pivot as a whole about a pivot connection 376 upward or downward as viewed in FIG. 9. Another pair of actuator wires (not shown) are connected with the base 374 to move the forceps/grasper assembly 352 to any selected position along a range of movement on a perpendicular axis.

In a similar manner, the surgical instruments illustrated in FIGS. 6, 7, and 8 are also freely positionable in the manner illustrated in FIG. 5. To this end, four actuator wires (not shown) are connected to the base 204 (FIG. 6) of the scissors assembly 202. Four actuator wires (not shown) are connected with the final link 140b (FIG. 7) of the articulated stem section 30b to move the final link and thereby the instrument 252, together, relative to the rigid stem section 16b. And in FIG. 8, four actuator wires (not shown) are connected with the base 304 of the basket cutter 302. The actuator wires of these devices are operable in the manner described with reference to FIGS. 1–5 to bend the articulated stem section 30b–30d to position the instruments with which they are connected.

From the above description of the invention, those skilled in the art will perceive improvements, changes and modifications in the invention. Such improvements, changes and modifications within the skill of the art are intended to be covered by the appended claims.

Having described the invention, we claim:

1. A surgical instrument comprising:

a manually engageable handle;

a rigid stem section extending from said handle;

tissue engaging means for engaging tissue, said tissue engaging means including first and second tissue engaging members, said first tissue engaging member being pivotable relative to said second tissue engaging member to engage tissue between said first and second tissue engaging members;

an articulated stem section connected between said rigid stem section and said tissue engaging means and supporting said tissue engaging means for three-dimensional movement between a plurality of orientations relative to said stem section;

first actuator means connected with said handle for bending said articulated stem section to change the orientation of said tissue engaging means relative to said stem section from a first orientation to a second orientation; and second actuator means connected with said handle and with said first tissue engaging member for effecting pivotal movement of said first tissue engaging member relative to said second tissue engaging member to engage tissue between said first and second tissue engaging members when said tissue engaging means is in any of its plurality of orientations relative to said stem section;

wherein said articulated stem section comprises a plurality of links and a plurality of pivot joints interconnecting said links for pivotal movement relative to each other about a plurality of axes.

2. A surgical instrument as set forth in claim 1 wherein said links are hollow generally cylindrical members through which extend a plurality of actuator wires, said actuator wires being connected between said second tissue engaging member and said actuator assembly, said actuator wires being selectively tensionable upon manual movement of said actuator assembly to move said second tissue engaging member between a plurality of positions.

3. A surgical instrument as set forth in claim 2 wherein said pivot joints define pivot axes extending in perpendicular directions and enabling multi-planar bending movement of said articulated stem section.

4. A surgical instrument as set forth in claim 3 wherein said tissue engaging means comprises a basket cutter including a movable jaw and a fixed jaw, said first tissue engaging member comprising said movable jaw and including a side wall defining an open-ended chamber, said second tissue engaging member comprising said fixed jaw and including a side wall defining a chamber having opposed open ends, said second actuator means comprising means for moving said movable jaw into said chamber in said fixed jaw to engage tissue between said movable and fixed jaws when said tissue engaging means is in any of its plurality of orientations relative to said stem section.

5. A surgical instrument as set forth in claim 4 wherein said first tissue engaging member side wall includes a cutting edge at least partially defining said open-ended chamber and being movable in sliding engagement against said side wall of said second tissue engaging member upon movement of said first tissue engaging member into said chamber in said second tissue engaging member.

6. A surgical instrument as set forth in claim 4 wherein said second actuator means comprises a flexible elongate member extending along said articulated stem section between said handle and said tissue engaging means, and a manually engageable second actuator member on said handle, said elongate member having a first end portion connected with said second actuator member and a second end portion connected with said first tissue engaging member.

7. A surgical instrument as set forth in claim 6 wherein said a flexible elongate member comprises a wire.

8. A surgical instrument as set forth in claim 6 wherein said second actuator member comprises a trigger supported for pivotal movement on said handle.

9. A surgical instrument comprising:

a manually engageable handle;

a rigid stem section extending from said handle;

tissue engaging means for engaging tissue, said tissue engaging means including a first tissue engaging member;

an articulated stem section connected between said rigid stem section and said tissue engaging means and supporting said tissue engaging means for three-dimensional movement between a plurality of orientations relative to said stem section;

pivot joint means for supporting said first tissue engaging member on said articulated stem section for pivotal movement relative to said articulated stem section;

first actuator means connected with said handle for bending said articulated stem section to change the orientation of said tissue engaging means relative to said rigid stem section from a first orientation to a second orientation; and second actuator means connected with said handle and with said first tissue engaging member for effecting pivotal movement of said first tissue engaging member relative to said articulated stem section to engage tissue when said tissue engaging means is in any of its plurality of orientations relative to said stem section;

wherein said articulated stem section comprises a plurality of links and a plurality of pivot joints interconnecting said links for pivotal movement relative to each other about a plurality of axes.

10. A surgical instrument as set forth in claim 9 wherein said pivot joints define pivot axes extending in perpendicular directions and enabling multi-planar bending movement of said articulated stem section.

11. A surgical instrument as set forth in claim 10 wherein said tissue engaging means comprises a basket cutter.

12. A surgical instrument comprising:

a manually engageable handle;

a rigid stem section extending from said handle;

tissue engaging means for engaging tissue, said tissue engaging means including a first tissue engaging member;

an articulated stem section connected between said rigid stem section and said tissue engaging means and supporting said tissue engaging means for three-dimensional movement between a plurality of orientations relative to said stem section;

pivot joint means for supporting said first tissue engaging member on said articulated stem section for pivotal movement relative to said articulated stem section;

first actuator means connected with said handle for bending said articulated stem section to change the orientation of said tissue engaging means relative to said rigid stem section from a first orientation to a second orientation; and second actuator means connected with said handle and with said first tissue engaging member for effecting pivotal movement of said first tissue engaging member relative to said articulated stem section to engage tissue when said tissue engaging means is in any of its plurality of orientations relative to said stem section.

said first actuator means comprising a single manually engageable control member which is mounted on said handle and which is movable to bend said articulated stem section to provide said three-dimensional movement of said tissue engaging means relative to said rigid stem section.

13. A surgical instrument as set forth in claim 12 wherein said articulated stem section supports said tissue engaging means for simultaneous movement relative to said rigid stem section about a first axis which extends perpendicular to a central axis of said rigid stem section and about a second axis which extends perpendicular to both said first axis and said central axis, said single manually engageable control member being movable in plurality of planes to move said tissue engaging means relative to said rigid stem section simultaneously about said first axis and said second axis.

* * * * *